United States Patent [19]
Nielsen

[11] Patent Number: 5,119,674
[45] Date of Patent: Jun. 9, 1992

[54] FLOWMETER

[76] Inventor: Paul V. Nielsen, Th. Nielsensvej 11, Faarevejle, DK-4540, Denmark

[21] Appl. No.: 603,684
[22] PCT Filed: Dec. 29, 1988
[86] PCT No.: PCT/DK88/00225
§ 371 Date: Oct. 31, 1990
§ 102(e) Date: Oct. 31, 1990
[87] PCT Pub. No.: WO89/11083
PCT Pub. Date: Nov. 16, 1989

[30] Foreign Application Priority Data
May 6, 1988 [DK] Denmark ............................. 2523/88

[51] Int. Cl.⁵ .................................................. G01F 1/68
[52] U.S. Cl. .................................. 73/204.24; 73/204.17
[58] Field of Search ........................... 73/204.17, 204.24

[56] References Cited

U.S. PATENT DOCUMENTS

| | | |
|---|---|---|
| 1,996,943 | 12/1929 | Wile . |
| 2,540,822 | 2/1951 | Hastings ........................ 73/204.24 |
| 2,745,283 | 5/1956 | Hastings ........................ 73/204.24 |
| 3,485,099 | 12/1969 | Collins ........................... 73/204.24 |
| 3,564,916 | 2/1971 | Collins ........................... 73/204.24 |
| 4,240,441 | 12/1980 | Khalil . | 
| 4,848,147 | 7/1989 | Bailey et al. .................. 73/204.17 |

FOREIGN PATENT DOCUMENTS 3135707 4/1982 Fed. Rep. of Germany .
3112144 10/1982 Fed. Rep. of Germany .
440700 8/1985 Sweden .

*Primary Examiner*—Herbert Goldstein
*Attorney, Agent, or Firm*—Scully, Scott, Murphy & Presser

[57] ABSTRACT

A flowmeter comprising a thermocouple with hot and cold junctions and a current source for causing a temperature difference between the hot and cold junctions of the thermocouple. The thermocouple is connected to the current source through a controlled switch, with a control input on the switch being connected to a control device. The control device also controls a measuring circuit, which on its input port receives a signal representing the e.m.f. of the thermocouple during the periods of time when the current from the current souce to the thermocouple is interrupted by the switch. The current source and the hot and cold junctions of the thermocouple all are connectable in series by the control device through the same two conductors which are also connected to the measuring circuit.

13 Claims, 4 Drawing Sheets

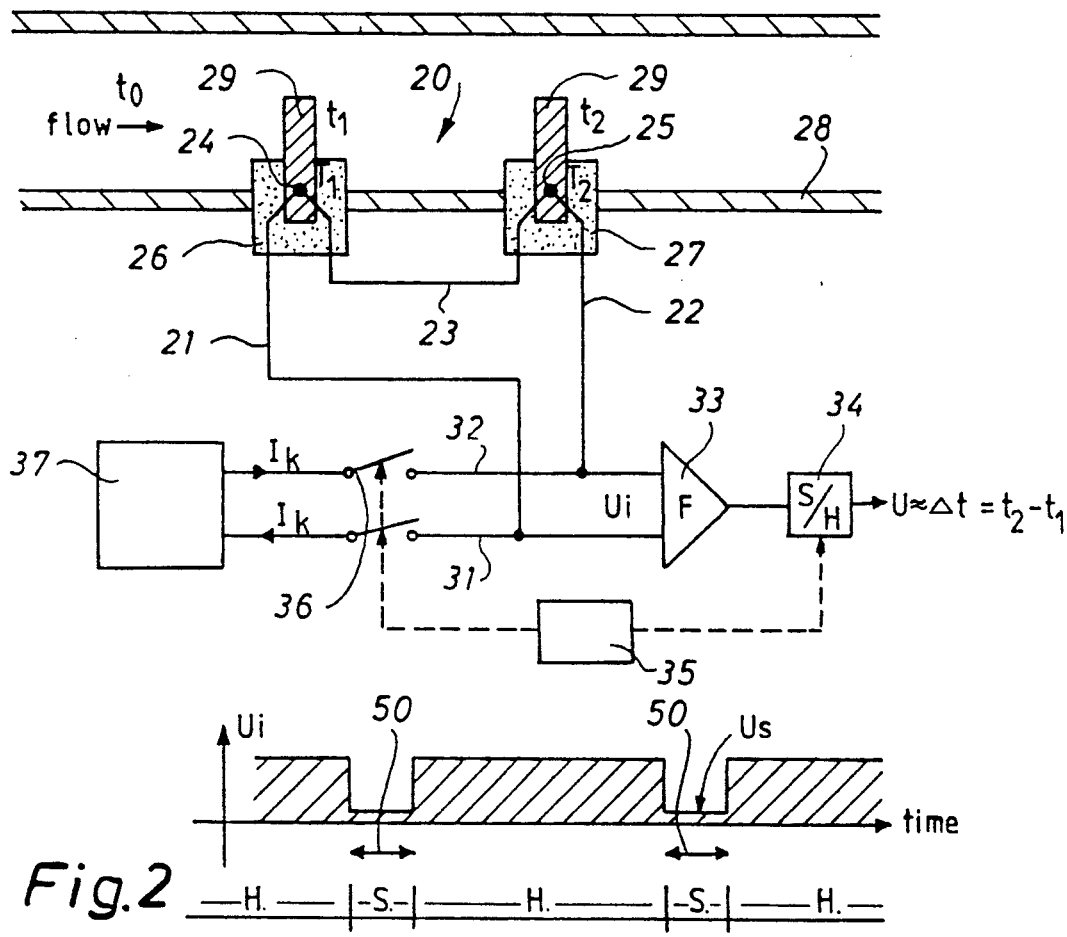
Fig.1
Fig.2
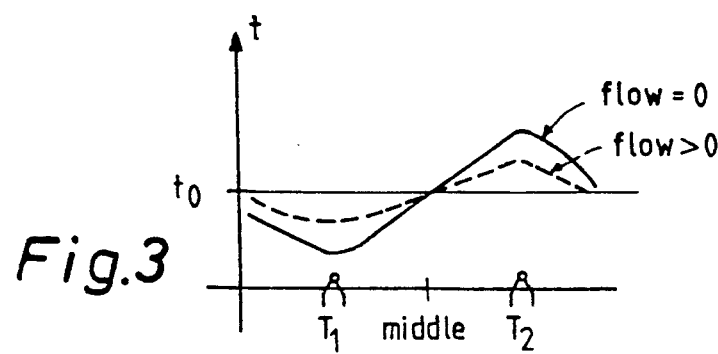
Fig.3

FLOWMETER

TECHNICAL FIELD

The present invention relates to a flowmeter comprising a thermocouple and a current source for causing a temperature difference between the two junctions of the thermocouple, and wherein the thermocouple is electrically communicating with the current source through a controlled switch alternately closing and breaking a current, and wherein a control input on the controlled switch is connected to a control device also controlling a measureing circuit, which on its input port receives a signal representing the e.m.f. of the thermocouple during the periods of time where the current from the current source to the thermocouple has been interrupted by the controlled switch.

BACKGROUND ART

U.S. Pat. No. 3,485,099 discloses a fluid flow responsive apparatus comprising a thermocouple having both its junctions in the fluid, and means for periodically heating one of the junctions. An output circuit responds to the thermocouple EMF produced between the heating periods. The thermocouple EMF depends on the rate of flow of the loss of heat at the heated junction and depends thus on the rate of flow of the fluid. Similar apparatuses are disclosed in DE-A No. 1,928,228, DE-A No. 1,648,006, U.S. Pat. No. 1,996,943, and U.S. Pat. No. 4,240,441. Typically the flowmeters comprise a probe including one or two thermocouples and a heating coil and reference means connected through a cable to associated electronic equipment including a current source, a control means, switching means, and measuring means.

Especially the medical industry presents a demand for very small probes and connecting cables to the flowmeters. All the known systems require several electrically conducting wires between the probe of the flowmeter and the associated electronic. Typically eight conductors are used in a connecting cable between a probe and the electronic equipment, as the heating coil, a reference means, and an active sensor all need connections including connections to the ground. In addition a demand has arisen for a diminution and preferably a complete omission of a supply of heat.

DISCLOSURE OF INVENTION

The object of the present invention is to provide a flowmeter comprising a particularly small probe with only two electrical conductors, and in particular a probe capable of measuring the blood flow in the cardiovascular system.

The flowmeter according to the invention is characterised in that the current source and the hot and the cold junction of said thermocouple all are connectable in series by the control device through the same two conductors also connected to the measuring circuit, and wherein the current source is a dc-source.

Due to the Seeback-effect the thermocouple acts per se as both a heating and a cooling member because one junction of the thermocouple is heated by the dc-current from the current source simultaneously with the other junction of said thermocouple being correspondingly cooled, whereby a temperature difference between the two junctions develops. During the periods of time where the controlled switch has interrupted the current from the current source, the thermocouple supplies a voltage representing the temperature difference caused. As the resulting temperature difference simultaneously depends on the flow velocity in the surroundings of the thermocouple, the output voltage of the thermocouple can be used for determining the flow velocity. The controlled switch renders it possible to use the same two wires for the supply of dc-current and consequently for the heating of the thermocouple as well as while the switch is interrupted for transferring the measurement signal. In this manner a probe with only two electrical conductors is obtained which allows production of a very small probe. An additional advantage of the above probe is that the net supply of heat to the observed fluid is zero.

According to a preferred embodiment of the invention the measuring circuit comprises an amplifier and/or a sample and hold circuit, and that the control device is a timer circuit.

According to a second embodiment of the invention the measuring circuit is such that it comprises an analogue-to-digital converter and a microprocessor associated with a clock generator, a memory, and in/outputs. By this embodiment the microprocessor may simultaneously constitute the control device controlling the switch.

According to a particularly simple embodiment of the invention, the flowmeter is characterised in that the thermocouple is included in a probe, and that the current source, the controlled switch, the amplifier, the sample and hold circuit, and the control device are combined in one or more separate units at a distance from the probe including the thermocouple only connected thereto through two conductors. In this manner a particularly simple probe is obtained, which may be very thin.

The thermocouple comprises typically a metal wire of a first metal connected in one junction with a metal wire of a second material which in turn in a second junction is connected to a metal wire of the first metal thereby providing a hot and a cold junction. According to a particularly advantageous embodiment a length of one of the metal wires, preferably the intermediary wire of the second metal, has been wound as a coil about a heat-conducting bar communicating by way of heat conductivity with the hot junction being heated by the current from the current source. As a result the junction in question is additionally heated and consequently the sensor becomes more sensitive at the expenses of a small supply of heat. The supply of heat is, however, still less than in connection with the known flowmeters of the calorimeter type.

The thermocouple is typically composed of copper, constantan, and copper, and a portion of the constantan wire may be thick having a low electrical resistance, whereas a second portion of the wire may be thinner than the first portion, said second portion being wound about the heat-conducting rod.

Other material combinations apply within the scope of the inventions, such as Fe/cu-Ni, Ni-Cr/Cu-Ni, Ni-Cr/Ni-Al-Mn-Si, Pt/Pt-Rh, C/SiC. Such combinations of materials must be selected in view of specific requirements presented to a specific purpose. Thus if the probe is intended to be put in contact with blood in living tissue, the latter presents specific requirements as to the non-toxicity and blood compatibility of the materials. Thus the scope of the invention allows the conducting portions of the probe to be coated with a tissue-compatible metal, such as silver or gold or a thin surface-treatment of another tissue-compatible material.

According to an embodiment of the invention the two conductors connecting the amplifier input with the probe are provided by a coaxial cable, and the probe comprises a copper bar or tube. The bar or tube is mounted axially aligned with the inner conductor of the coaxial cable and is surrounded by a heating coil of constantan wire, which simultaneously connect the outer end of the copper bar and consequently the probe with the outer conductor of copper in the coaxial cable.

According to another embodiment of the invention the thermocouple is a Peltier device, i.e. the thermocouple is made of one or more semiconducting materials.

In a further embodiment of the invention an ac-source can be replaced by the dc-source. As a result it is possible to determine the direction of the flow, cf. the following explanation.

BRIEF DESCRIPTION OF DRAWINGS

The invention is described in greater detail below with reference to the accompanying drawings, in which FIG. 1 illustrates the fundamental structure of a particularly simple embodiment of a flowmeter according to the invention, FIG. 2 illustrates a diagram showing the input voltage versus the time at an amplifier input of the flowmeter of FIG. 1, FIG. 3 illustrates a diagram showing the temperatures in the flowmeter probe of FIG. 1.

BEST MODE FOR CARRYING OUT THE INVENTION

Figure 4:
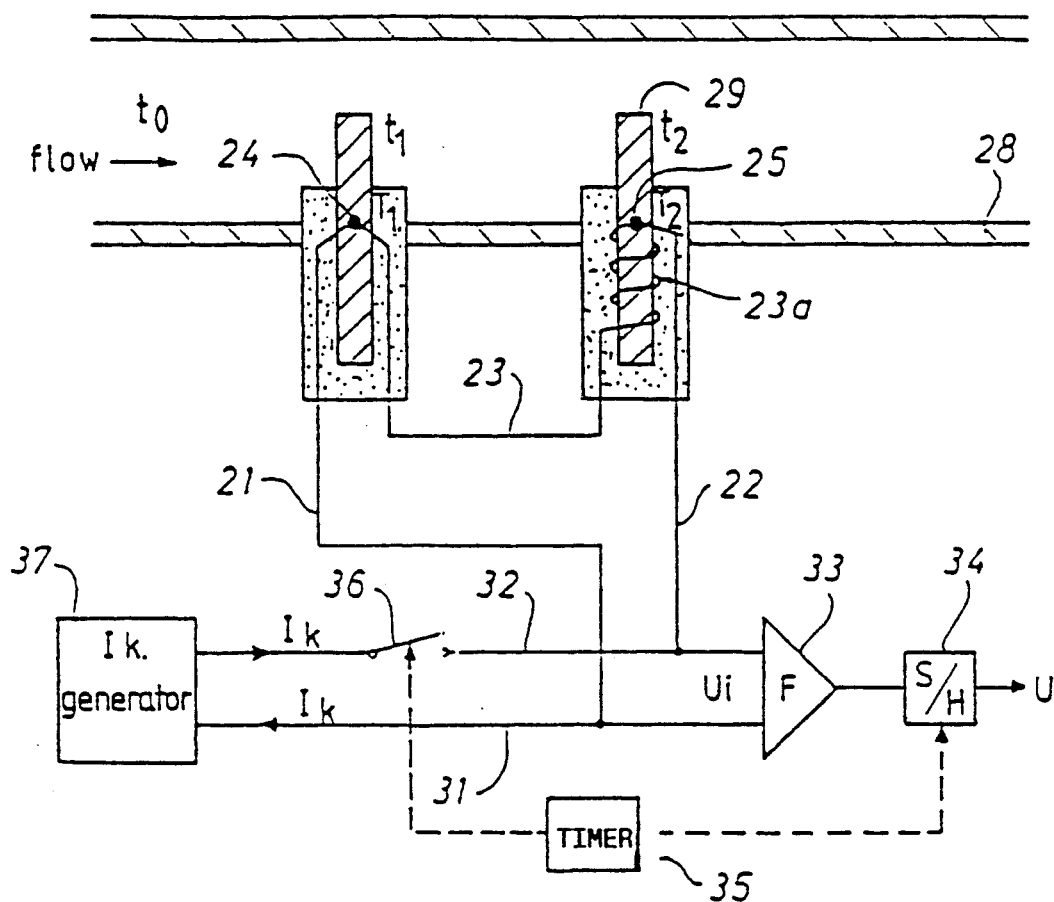
FIG. 4 illustrates the fundamental structure of a second embodiment of a flowmeter according to the invention.

FIG. 1 illustrates an example of the fundamental structure of a particularly simple embodiment of the flowmeter comprising a probe 20 according to the invention. The probe comprises a copper wire 21 welded to one end of a thick constantan wire 23 at a junction 24. The opposite end of the thick constantan wire 23 is welded to yet another copper wire 22 at a second junction 22. The junctions 24, 25 are connected to heat-conducting materials, such as copper bars 29. Each copper bar 29 projects into a tube 28 with a flowing fluid, the flow velocity of which is to be measured. The entire probe is surrounded by a material 26, 27 which is electrically insulating as well as heat insulation and allowing the positioning of the probe in the tube 28.

The constantan wire 23 has been mentioned as "thick" because it must be capable of conducting a current which is so heavy that the temperature of the junctions alters noticeably. However, in practise the constantan wire is not particularly thick.

The two copper wires 21, 22 are connected to their respective conductors 31, 32 in turn connected to the input port of an amplifier 33. The output port of the amplifier 33 is coupled to a sample and hold circuit 34. The output voltage U of the circuit 34 is a measurement of the temperature difference $T = T2 - T1$, where T1 and T2 represent the temperature of the two junctions 24, 25. A control device 35, such as a timer, controls a switch 36 enabling and disabling a current in the conductors 31, 32 which are connected to a source 37 of constant current. The switch 36 is preferably an electronic switch, such as a transistor, and may for instance be an FET.

The flowmeter operates in the following manner:

The timer 35 closes the switch 36 whereafter a current flows from the current source 37 through the conductor 32, the copper wire 22, the junction 25, the constantan wire 23, the junction 24, the copper wire 21, and the conductor 31 back to the current source 37. While the current is flowing through said circuit, the first junction is heated and the second junction is cooled due to the Seeback-effect. The amount of heat and cold, respectively, produced per sec. is proportional to the electric current $I_K$. If the temperature of the flowing liquid is called T0, the temperature of the cold junction T1, and the temperature of the hot junction T2, the following relation applies:

$$T0 - T1 = T2 - T0 = K_a \times I_K.$$

where $K_a$ is a constant depending on the thermal conditions on the site and the thermocouple used. $I_K$ is the current through the thermocouple. After a predetermined period of time the timer 35 opens the switch 36 and the current to the junctions 24, 25 is interrupted. Now the respective temperature T1 and T2 of the two junctions 24, 25, respectively, differ and consequently the thermocouple exhibits an electromotive force whereby a voltage develops between the conductors 31 and 32 and consequently on the input port of the amplifier 33. The difference in voltage is amplified in the amplifier 33, and the amplified signal is transferred to the sample and hold circuit 34. The latter circuit 34 is controlled by the timer 35 in such a manner that the holding circuit stores the signal, i.e. the thermal voltage $U_s$, only in the time interval 50 where the switch 36 is open. The voltage $U_i$ on the input port of the amplifier has been illustrated versus the time by means of the diagram of FIG. 2, and immediately below said diagram the corresponding sampling periods S and holding periods H for the sample and hold circuit are indicated. The relatively low voltage $U_s$ is the thermal e.m.f. applying in the short time interval 50 when the switch 36 is open.

As illustrated in FIG. 1, the two junctions 24 and 25 communicate by way of heat conductivity with the interior of the tube 28. FIG. 3 illustrates the temperatures at the junctions 24, 25 the by way of the fully drawn curve line of the diagram when the flow velocity of the fluid or the gas in the tube is zero. As it is well-known from the calorimeter flowmeters, the flowing fluid diminishes the temperature difference caused between the two junctions 24, 25 when the flow velocity differs from zero. A non-zero flow velocity results therefore in a temperature curve as indicated by a dotted line. The stronger the current is, the smaller the temperature difference achieved. Therefore the temperature difference can be used as a measurement of the flow velocity inside the tube 28.

The above flowmeter is advantageous in only needing two conductors to the probe unlike a similar, known probe where the temperature difference between the two junctions is caused by a heating member situated at one junction. The known heating member requires a separate supply of voltage through separate conductors.

A particular advantage of the flowmeter according to the invention is that the total supply of heat energy to the fluid flow in the preferred embodiments is zero, i.e. one junction is cooled just as much as the other junction is heated. Such a supply of heat energy through a measuring probe is undesired in many cases.

FIG. 4 illustrates a further development of the principle of FIGS. 1 to 3. All the corresponding members of FIG. 4 are provided with the same reference numerals as in FIG. 1 and are therefore not described again. The embodiment of FIG. 4 differs from FIG. 1 by the thick constantan wire 23 continuing into a thinner wire 23a wound about the heat-conducting bar 29, said wire 23a being a heating member of a predetermined resistance R. The heating wire 23a is connected to the copper wire 22 at the junction 25. The constantan wire 23 can also be a long relatively thin wire substantially constant in diameter. The switch 36 is here shown as a unipolar switch merely breaking the current circuit through the current source.

Figure 5:
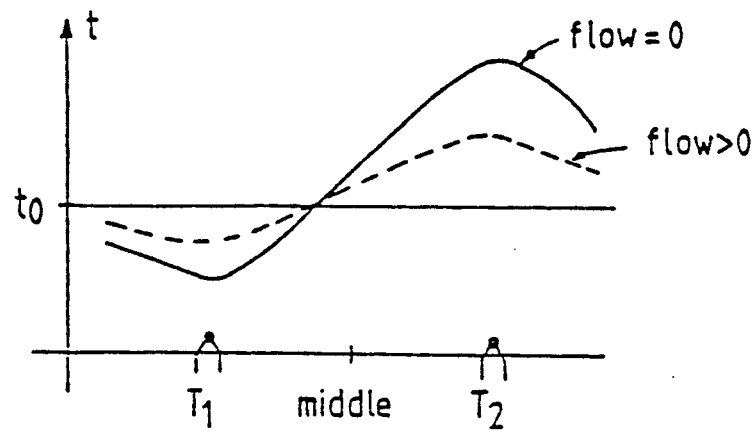
FIG. 5 illustrates a diagram showing the temperatures of the flowmeter of FIG. 4.

The solid curve of FIG. 5 illustrates the temperatures of the liquid or the gas inside the tube 28 at a flow velocity of zero. The temperature at the cold junction is determined by $T0 - T1 = K_a \cdot I_K$, and the temperature T2 at the hot junction can be determined by the equation $$T2 - T0 = K_a \cdot I_K + K_b \cdot (R \cdot I_K 2)$$

where Ka is still a constant depending on the thermocouple used and the thermal conditions on site, and $K_b$ is a second constant depending on the thermal conditions about the bar 29, whereas R is the resistance in the length of the constantan wire forming the heating member about the bar 29. A flow velocity exceeding zero results in a diminishing of the temperature difference, cf. the dotted curve. As a consequence thereof and like the previous example, the temperature difference achieved between the two junctions presents a measurement of the flow velocity.

The associated measuring circuit may be identical with the circuit described in connection with FIG. 1. The probe shown in FIG. 4 and the associated heating member is more sensitive than the probe of FIG. 1. Also the probe of FIG. 4 requires only two conductors between the probe and the measuring circuit. The flowing liquid is supplied with less heat energy than in connection with the known flowmeters.

Figure 6:
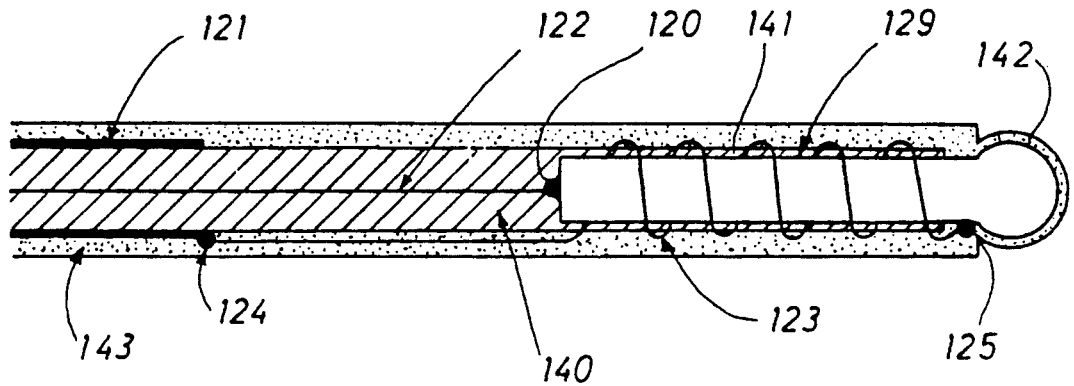
FIG. 6 illustrates an embodiment of a probe for a flowmeter according to the invention.

A practical embodiment of a probe is described below with reference to FIG. 6. The probe utilizes the measuring principle described diagrammatically in the above example. The embodiment of FIG. 6 is particularly suited for measuring the flow velocity in thin tubes, such as in the cardiovascular system of a human being.

The Figure illustrates only the probe situated at the end of a 1.2 mm coaxial cable. The inner conductor 122 of the cable is connected in one junction 120 to one end of a copper bar or tube being "thick" relative to the inner conductor and of a diameter of for instance about 1 mm and forming the heat-conducting material 129. At the opposite end of the copper bar in a "hot" junction 125, the copper bar is connected to a constantan wire 123 wound about the copper bar and consequently forming a heating coil. The constantan wire 123 ends in a "cold" junction 124, where it is connected to the outer conductor of copper 121 of the coaxial cable. The outer conductor 121 and the inner conductor 122 are insulated in a conventional manner from one another by an insulating material 140 and are surrounded by an outer plastic cable sheathing 143. The heating coil 123 and the copper bar 129 have also been electrically insulated as indicated in the drawing by a layer 141 which may be an insulating lac or a thin plastic coating. In view of the desired heat transmission from the heating coil 123 to the copper bar 129, the electrically insulating layer should be chosen so thin that it does not prevent the transmission of heat to a significant degree.

The end of the probe is surrounded by a thin electrically insulating, but heat-conducting layer 142, and the entire probe is surrounded by a cable sheathing 143 completely or partially being the plastic cable sheathing of the cable.

The opposite end of the coaxial cable is connected to the electronic supply of current and to the measuring circuit, which may be built like the circuit of FIG. 1, but wherein the conductors 21, 22 have been replaced by the cable 121, 122. The cable including the flowmeter probe can be used for measuring arterial blood flow in himan beings. Such a measurement can inter alia be used for determining how far an arteriosclerosis has advanced.

Figure 7:
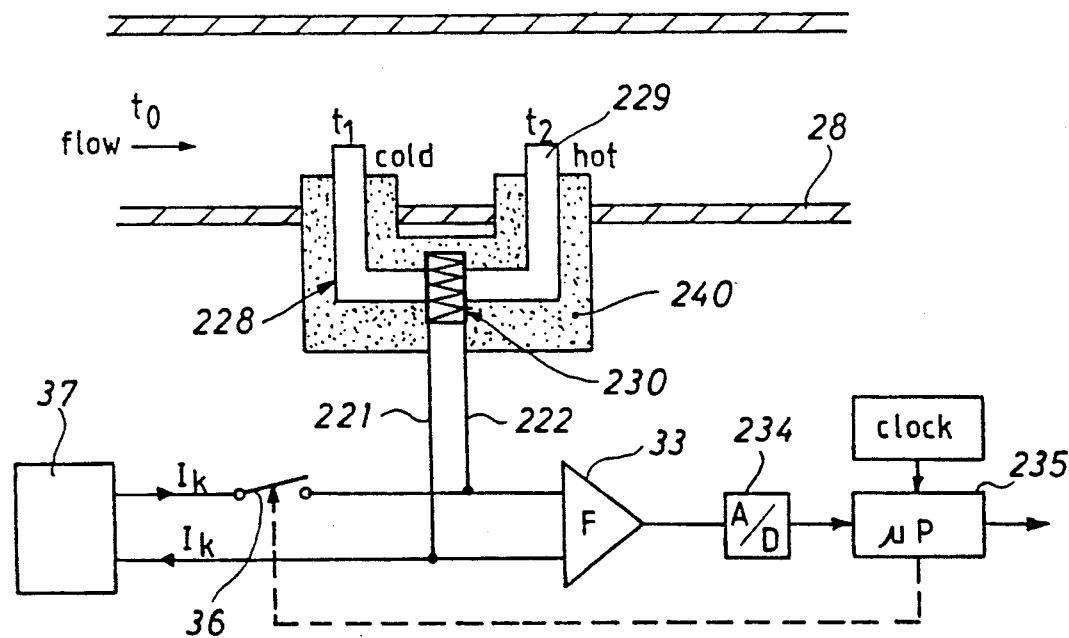
FIG. 7 illustrates an example of a probe comprising a semiconductor.

Yet another embodiment according to the invention is shown in FIG. 7, where the probe comprises a semiconducting thermocouple, also called a Peltier member. The probe of FIG. 7 comprises two heat-conducting metal loops 228, 229 abutting their respective side of a semiconductor Peltier member 230. The entire probe is surrounded by a heat-insulating material 240. The connecting wires 221, 222 are at one end connected to their respective side of the semiconductor Peltier member and at the opposite end to a measuring circuit and a current source. The measuring circuit may be as shown in FIGS. 1 and 4, but according to an alternative embodiment, cf. FIG. 7, the measuring circuit comprises an analogue-to-digital converter 234 converting the voltage signal from the thermocouple into a digital signal transmitted to a microprocessor 235. The microprocessor 235 may be such that one of the output ports thereof can be used for controlling the electronic switch 36. The microprocessor 235 is adapted so as to transmit an output signal representing the flow velocity.

In principle the semiconductor Peltier member acts as any other thermocouple: When an electric current is transmitted through the member, it turns cold on one side surface and hot on the opposite side surface. When the member is not connected to a current source, and when a temperature difference between the two side surfaces exists, the member indicates a voltage proportional to the temperature difference $\Delta T$. The sensitivity achievable by the semiconductor Peltier member is better than the sensitivities achievable by means of metallic thermocouples because both the resulting temperature difference in °C. per ampere at cooling/heating and the resulting output voltage in volt per °C. in the temperature difference are far better for the semiconductor Peltier member than for the metallic thermocouple.

Figure 8:
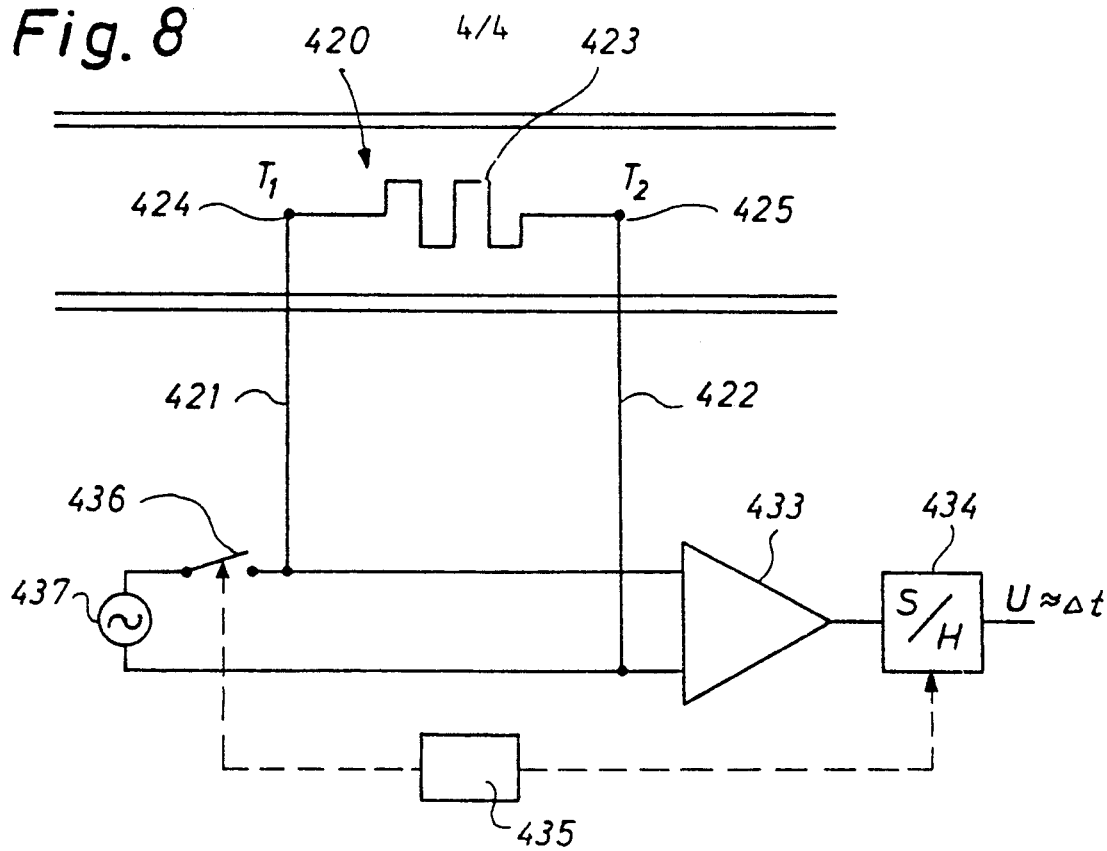
FIG. 8 illustrates a further embodiment of the invention.

According to a particular embodiment and a principle shown in FIG. 8, a flowmeter comprises a thermocouple 420. The thermocouple comprises a copper conductor 421 welded to one end of a constantan wire 423 at a junction 242, and a second copper conductor 422 welded to the opposite end of the constantan wire 423 at a second junction 425. The constantan wire 423 has been wound as a heating member and preferably helically and is situated substantially in the middle between the two junctions 424 and 425. The heating member must at least be spaced from at least one junction. The temperature difference mentioned below is caused solely by the heating by the heating member.

The two copper conductors 421 and 422 are coupled to an electronic circuit which may be identical with the measuring circuit of FIG. 1, and which therefore need no further mentioning here. The only alteration is that while the current source 37 of FIG. 1 is meant to be a DC current source, the current source 437 is an AC current source, preferably a square wave-current source allowing adjustment of the amplitude. It is assumed below that the mean value of the current is zero or in other words that the current is equally strong in both directions (alternately). The slowness of the thermocouple has the effect that such an alternating current of a suitable high frequency through the conductors 431, 432, the switch 436, and the conductors 421, 422, 423 per se involves no temperature difference between the two junctions, but it heats the heating wire 423.

After a predetermined heating period H the switch 436 controlled by a timer 435 opens, and during the following measuring period S a possible temperature difference between the junctions 424, 425 causes a thermo e.m.f. Us. The thermo e.m.f. is amplified in the amplifier 433 and can be detected by means of the sample and hold circuit.

If we assume that the heating member 432 is situated in the middle between the two junctions, and that the structure is substantially symmetrical and filled with the same fluid, the heat from the heating member spreads to the same degree and at the same speed to both sides towards the junctions, which are therefore still of the same temperature. The symmetry is maintained as long as the flow inside the tube is zero. If there is a flow of fluid in the tube, said flow of fluid carries heat from the heating member to one junction which is consequently heated. As a result a temperature difference Δt exists between the two junctions and during the following measuring period S, the electric current direction or the sign of the electric voltage signal from the thermocouple indicates the direction of the fluid flow inside the tube. As a result, a flow-direction-meter indicating the flow direction is obtained.

Figure 9:
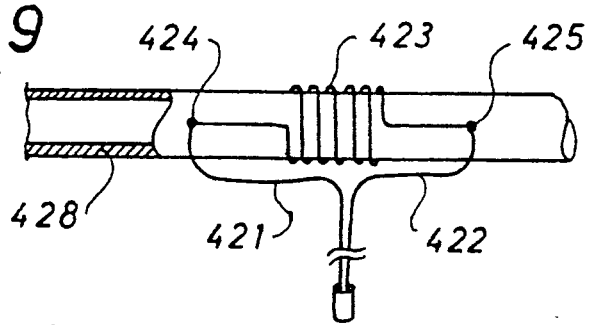
FIG. 9 illustrates a detailed embodiment of a probe for the flowmeter of FIG. 8.

The above flow-direction-meter can be manufactured in many embodiments, and FIG. 9 illustrates an embodiment thereof to be used for industrial plants where the heating wire 432 has been wound about a heat-conducting tube 428. The latter tube can receive the fluid flow to be measured, and the junctions 424, 425 are mounted on each side of the heat winding 423 on the outside of the tube 428.

Figure 10:
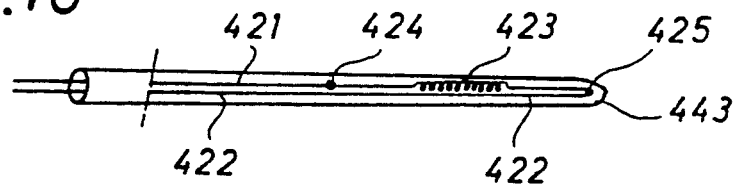
FIG. 10 illustrates a further embodiment of the invention.

According to a second embodiment to be used in hospitals for measuring directly on a patient, such as for measuring the blood flow, the probe can be manufactured so as to be insertable in the vein as outlined in FIG. 10. 443 is a thin electrically insulating, tissue-compatible cable sheathing, and the cable sheathing with the conductors 421, 422 and the junctions and heating member can be manufactured so as to be of a diameter of for instance 2 mm and preferably less.

Figure 11:
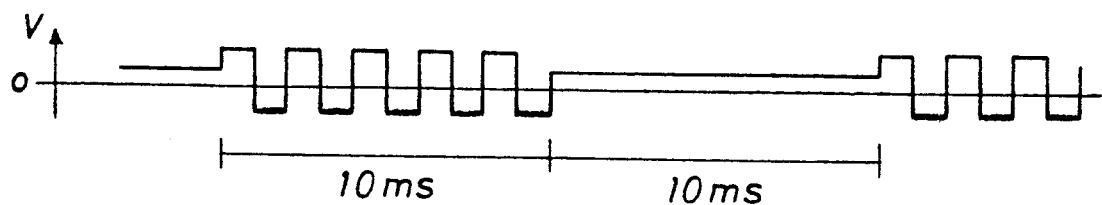
FIG. 11 shows the voltage across the thermocouple versus the time.

The frequency of the alternating current used can for instance be 500 Hz or 1 kHz and a duration of for instance 10 msec. of the period in which the alternating current is applied to the heating member. FIG. 11 illustrates the voltage across the thermocouple versus the time.

The above described embodiments can be combined in various manners, and according to a particularly advantageous embodiment it is possible by combining a DC current source with an AC current source to measure both intensity and direction of a fluid flow. The latter is achieved for instance by initially coupling the DC current source to the flowmeter so as to determine the amount of the flow and then exchanges said DC current source with an AC current source so as to determine the flow direction or vice versa.

When a non-symmetric flowmeter is used, i.e. when the heating wire is closer to one junction than the other, it is still possible to determine the flow direction: A flow is assumed from the left towards the right at the probe of FIG. 4, and a heating period H involving an alternating current results in a strong heating of the junction 425, whereas the junction 424 is of the same temperature as the liquid or gas inside the tube 428. The temperature difference between the two junctions causes a substantial thermo e.m.f. in the following measuring period S on the input port of the amplifier 433 and consequently an output voltage from the sample and hold circuit 434.

If the fluid flow in the tube shown in the same FIG. 4 is from the right towards the left, a corresponding heating period H including an alternating current supply results still in a strong heating of the junction 425, and now the junction is heated to some extent in response to the heat-conducting capability of the fluid flow. The latter means that the temperature difference between the two junctions in this situation is smaller and consequently causes a lower thermo e.m.f. on the input port of the amplifier 433 and consequently a lower voltage on the output of the sample and hold circuit 434. Even in case of an unsymmetric probe it is therefore possible to determine the flow direction by using an alternating current source for the heating.

A flowmeter according to the invention may be used within many fields. It can be very small and is therefore suitable for use inside the medical field. High-explosive environments present another potential field of application because the probe per se is only supplied with a very low voltage. The associated electronic circuit can be situated outside the high-explosive area.

It is obvious to persons skilled in the art that the above invention can be altered in many ways without thereby deviating from the scope of the attached claims. For instance the intermediary metal wire is not necessarily a thick constantan wire or a combination of a thick and a thin constantan wire. It may very well be a rather thin wire of which a substantial length has been wound as a heating member about a semiconducting bar at the hot junction. The heat-conducting bars may also be larger or smaller and may optionally be completed omitted, because the junctions per se can constitute the heat-sensitive points instead of the bars and the metal wire thermocouple may be substituted by a solid state Peltier member.

I claim:

1. A flowmeter comprising, a thermocouple having a hot junction and a cold junction with both the hot junction and the cold junction being located in and exposed equally to a fluid flow, a DC current source for causing a temperature difference between the hot and cold junctions of the thermocouple, a controlled switch electrically coupling the thermocouple with the DC current source and being alternately closed and opened to interrupt the current therethrough, a measuring circuit, and a control device, wherein a control input of the controlled switch and a control input of the measuring circuit are coupled to the control device which controls both the controlled switch and the measuring circuit, which on its input port receives a signal representing the e.m.f. of the thermocouple during the periods of time when the current from the current source to the thermocouple is interrupted by the controlled switch, and further wherein the current source and the hot and the cold junctions of the thermocouple are all connectable in series by the controlled switch under control of the control device through the same two conductors which are also connected to the measuring circuit.

2. A flowmeter as claimed in claim 1, wherein the measuring circuit comprises an amplifier and a sample and hold circuit, and wherein the control device is a timer circuit.

3. A flowmeter as claimed in claim 1, wherein the measuring circuit comprises an analogue-to-digital converter, a microprocessor associated with a clock generator, a memory, and inputs and outputs.

4. A flowmeter as claimed in claim 3, wherein the microprocessor comprises the control device controlling the controlled switch.

5. A flowmeter as claimed in claim 2, wherein the thermocouple is included in a probe, and wherein the current source, the controlled switch, the amplifier, the sample and hold circuit, and the control device are combined in a number of separate units at a distance from the probe and are connected thereto by only two conductors.

6. A flowmeter as claimed in claim 1, wherein the thermocouple comprises a metal wire of a first metal connected in one junction with a metal wire of a second material which is connected in a second junction to a metal wire of the first metal thereby providing the hot and cold junctions, and wherein a length of one of the metal wires is wound as a coil about a heat-conducting bar communicating by heat conductivity with the hot junction which is heated by current from the current source.

7. A flowmeter as claimed in claim 6, wherein the thermocouple is made of copper, constantan and copper, and wherein a length of constantan wire is wound about the heat-conducting bar.

8. A flowmeter as claimed in claim 6, wherein the thermocouple is included in a probe, and the measuring circuit comprises an amplifier and a sample and hold circuit, and wherein the current source, the controlled switch, the amplifier, the sample and hold circuit, and the control device are combined in a number of separate units at a distance from the probe which are connected thereto by two conductors, and wherein the thermocouple is made of copper, constantan and copper, with a length of constantan wire being wound as a heating coil around the heat-conducting bar, and wherein the two conductors are provided by a coaxial cable, the inner conductor thereof continuing to the heat conducting bar which is made of copper, wound with the heating coil of constantan wire, which continues to the outer screen of copper of the coaxial cable.

9. A flowmeter as claimed in claim 1, wherein the thermocouple comprises a semiconducting Peltier device.

10. A flowmeter as claimed in claim 1, wherein the thermocouple comprises a metal wire of a first metal connected in one junction with a metal wire of a second material which is connected in a second junction to a metal wire of the first metal thereby providing the hot and cold junctions, and wherein a length of the intermediary wire of the second metal is wound as a coil about a heat-conducting bar communicating by heat conductivity with the hot junction which is heated by current from the current source.

11. A flowmeter as claimed in claim 2, wherein the thermocouple comprises a metal wire of a first metal connected in one junction with a metal wire of a second material which is connected in a second junction to a metal wire of the first metal thereby providing the hot and cold junctions, wherein a length of one of the metal wires is wound as a coil about a heat-conducting bar communicating by heat conductivity with the hot junction which is heated by current from the current source.

12. A flowmeter as claimed in claim 2, wherein the thermocouple comprises a metal wire of a first metal connected in one junction with a metal wire of a second material which is connected in a second junction to a metal wire of the first metal thereby providing the hot and cold junctions, and wherein a length of the intermediary wire of the second metal is wound as a coil about a heat-conducting bar communicating by heat conductivity with the hot junction which is heated by current from the current source.

13. A flowmeter comprising, a thermocouple having a hot junction and a cold junction with both the hot junction and the cold junction being located in and exposed equally to a fluid flow, an AC current source for causing a temperature difference between the hot and cold junctions of the thermocouple, a controlled switch electrically coupling the thermocouple with the AC current source and being alternately closed and opened to interrupt the current therethrough, a measuring circuit, and a control device, wherein a control input of the controlled switch and a control input of the measuring circuit are coupled to the control device which controls both the controlled switch and the measuring circuit, which on its input port receives a signal representing the e.m.f. of the thermocouple during the periods of time when the current from the current source to the thermocouple is interrupted by the controlled switch, and further wherein the current source and the hot and the cold junctions of the thermocouple are all connectable in series by the controlled switch under control of the control device through the same two conductors which are also connected to the measuring circuit.

* * * * *